United States Patent [19]

Roberts et al.

[11] Patent Number: 5,126,344
[45] Date of Patent: Jun. 30, 1992

[54] DIAZINE DERIVATIVES AND PHARMACEUTICAL USE

[75] Inventors: David A. Roberts, Congleton; Robert J. Pearce; Robert H. Bradbury, both of Wilmslow; Richard W. A. Luke, Macclesfield, all of England

[73] Assignee: Imperial Chemical Industries PLC, London, England

[21] Appl. No.: 615,753

[22] Filed: Nov. 19, 1990

[30] Foreign Application Priority Data

Nov. 20, 1989 [GB] United Kingdom ........... 8926211
May 21, 1990 [GB] United Kingdom ........... 9011348

[51] Int. Cl.$^5$ ............... A61K 31/435; A61K 31/495; C07D 221/00; C07D 487/02
[52] U.S. Cl. .................... 514/248; 514/249; 514/250; 514/258; 514/267; 514/293; 514/299; 544/238; 544/250; 544/279; 544/344; 544/350; 546/83; 546/122; 546/123
[58] Field of Search ........... 544/238, 250, 279, 344, 544/350; 546/122, 83, 123; 514/250, 258, 267, 249, 248, 293, 299

[56] References Cited

U.S. PATENT DOCUMENTS 4,820,843  4/1989  Aldrich et al. ............ 548/252
4,880,804  11/1989  Carini et al. ............ 514/234.5

FOREIGN PATENT DOCUMENTS 0253310  1/1988  European Pat. Off. .
0323841  7/1989  European Pat. Off. .
0410762  1/1991  European Pat. Off. .
3907937  9/1990  Fed. Rep. of Germany .

Primary Examiner—Richard L. Raymond
Attorney, Agent, or Firm—Thomas E. Jackson

[57] ABSTRACT

The invention concerns pharmaceutically useful novel compounds of the formula I, in which ring B, $R^1$, $R^2$, $R^3$, $R^4$, $R^5$, X and Z have the various meanings defined herein, and their non-toxic salts, and pharmaceutical compositions containing them. The novel compounds are of value in treating conditions such as hypertension and congestive heart failure. The invention further concerns processes for the manufacture of the novel compounds and the use of the compounds in medical treatment.

13 Claims, No Drawings

DIAZINE DERIVATIVES AND PHARMACEUTICAL USE

This invention concerns novel diazine derivatives and, more particularly, novel azaquinoline derivatives which possess pharmacologically useful properties in antagonising, at least in part, one or more of the actions of the substances known as angiotensins, and in particular of that known as angiotensin II (hereafter referred to as AII). The invention also concerns pharmaceutical compositions of the novel compounds for use in treating diseases or medical conditions such as hypertension, congestive heart failure and/or hyperaldosteronism in warm-blooded animals (including man), as well as in other diseases or medical conditions in which the renin-angiotensin-aldosterone system plays a significant causative role. The invention also includes processes for the manufacture of the novel compounds and their use in treating one of the afore-mentioned diseases or medical conditions and for the production of novel pharmaceuticals for use in such medical treatments.

The angiotensins are key mediators of the renin-angiotensin-aldosterone system, which is involved in the control of homeostasis and fluid/electrolyte balance in many warm-blooded animals, including man. The angiotensin known as AII is produced by the action of angiotensin converting enzyme (ACE) on angiotensin I, itself produced by the action of the enzyme renin on the blood plasma protein angiotensinogen. AII is a potent spasmogen especially in the vasculature and is known to increase vascular resistance and blood pressure. In addition, the angiotensins are known to stimulate the release of aldosterone and hence result in vascular congestion and hypertension via sodium and fluid retention mechanisms. Hitherto there have been a number of different approaches to pharmacological intervention in the renin-angiotensin-aldosterone system for therapeutic control of blood pressure and/or fluid/electrolyte balance, including, for example, inhibiting the actions of renin or ACE. However, there remains a continuing need for an alternative approach because of the side-effects and/or idiosyncratic reactions associated with any particular therapeutic approach.

Certain substituted imidazoles and benzimidazoles disclosed in European Patent Application, publication no. 253310 A2 and U.S. Pat. No. 4,880,804 respectively are described therein as inhibitors of the action of angiotensin II. Also certain substituted pyrroles, pyrrazoles and triazoles are described in European Patent Application, publication no. 323841 A2 as possessing AII antagonist activity.

We have now discovered that the compounds of the invention (set out below) surprisingly antagonise one or more of the actions of the substances known as angiotensins (and in particular of AII) and thus minimise the physiological effects associated with their presence in warm-blooded animals (including man) and this is the basis of the invention.

According to the invention there is provided an azaquinoline derivative of the formula I (set out hereinafter, together with the other chemical formulae identified by Roman numerals) wherein: ring B is a pyridine, pyridazine, pyrimidine or pyrazine moiety; $R^1$ is hydrogen, (1–8C)alkyl, (3–8C)cycloalkyl, (3–8C)cycloalkyl-(1–4C)alkyl, phenyl, phenyl(1–4C)alkyl or (1–4C)alkyl bearing one or more fluoro substituents; $R^2$ is hydrogen, (1–8C)alkyl, (3–8C)cycloalkyl, (3–8C)cycloalkyl-(1–4C)alkyl, carboxy, (1–4C)alkoxycarbonyl, cyano, nitro, phenyl or phenyl(1–4C)alkyl; $R^3$ and $R^4$ are independently selected from hydrogen, (1–4C)alkyl, (1–4C)alkoxy, fluoro(1–4C)alkoxy, halogeno, trifluoromethyl, cyano, nitro, hydroxy, amino, alkylamino and dialkylamino of up to 6 carbon atoms, carboxy, (1–4C)alkoxycarbonyl, carbamoyl and N-alkylcarbamoyl and di-(N-alkyl)carbamoyl of up to 7 carbon atoms; or when ring B is a pyridine moiety, $R^3$ and $R^4$ may optionally together form a (1–4C)alkylenedioxy group; $R^5$ is hydrogen, (1–4C)alkyl, (1–4C)alkoxy, halogeno, trifluoromethyl, cyano or nitro; X is phenylene optionally bearing a substituent selected from (1–4C)alkyl, (1–4C)alkoxy, halogeno, trifluoromethyl, cyano and nitro, or X is a direct bond between the adjacent phenyl and methylene groups; Z is 1H-tetrazol-5-yl, —CO.NH.(1H-tetrazol-5-yl) or a group of the formula —CO.O$\overline{R}^6$ or —CO.NH.SO$_2$.$R^7$ in which $R^6$ is hydrogen or a non-toxic, biodegradable residue of a physiologically acceptable alcohol or phenol, and $R^7$ is (1–6C)alkyl, (3–8C)cycloalkyl or phenyl; and wherein any of said phenyl moieties may be unsubstituted or bear one or two substituents independently selected from (1–4C)alkyl, (1–4C)alkoxy, halogeno, cyano and trifluoromethyl; or a physiologically acceptable salt thereof.

It will be appreciated that, depending on the nature of the substituents, certain of the formula I compounds may possess one or more chiral centres and may be isolated in one or more racemic or optically active forms. It is to be understood that this invention concerns any form of such a compound of formula I which possesses the afore-mentioned useful pharmacological properties, it being well known how to make optically active forms, for example by synthesis from suitable chiral intermediates, and how to determine their pharmacological properties, for example by use of the standard tests described hereinafter.

It is to be understood that generic terms such as "alkyl" include both straight and branched chain variants when the carbon numbers permit. However, when a particular radical such as "propyl" is given, it is specific to the straight chain variant, branched chain variants such as "isopropyl" being specifically named where intended. The same convention applies to other radicals.

A particular value for $R^1$ or $R^2$ when it is alkyl is, for example, methyl, ethyl, propyl, butyl, isobutyl, sec-butyl, pentyl or hexyl; when it is cycloalkyl is, for example, cyclopropyl, cyclopentyl or cyclohexyl; when it is cycloalkyl-alkyl is, for example, cyclopropylmethyl, cyclopentylmethyl, cyclohexylmethyl or 2-cyclopentyl-ethyl; when it is phenylalkyl is, for example, benzyl, 1-phenylethyl or 2-phenylethyl.

A particular value for $R^1$ when it is alkyl bearing one or more fluoro substituents is, for example, fluoromethyl, trifluoromethyl, 2,2,2-trifluoroethyl or pentafluoroethyl; and for $R^2$ when it is alkoxycarbonyl is, for example, methoxycarbonyl, ethoxycarbonyl or propoxycarbonyl.

Particular values for $R^3$, $R^4$, $R^5$ or for an optional substituent which may be present when X is phenylene, include, by way of example:

for alkyl, methyl and ethyl; for alkoxy, methoxy, ethoxy and isopropoxy; for fluoroalkoxy: trifluoromethoxy, 2-fluoroethoxy, 2,2,2-trifluoroethoxy and 3,3,3-trifluoropropoxy; for halogeno, fluoro, chloro, bromo and iodo; for alkylamino: methylamino, ethylamino and butylamino; for dialkylamino: dimethylamino, diethylamino and dipropylamino; for N-alkylcarbamoyl: N-methyl and N-ethylcarbamoyl; for di(N-alkyl)carbamoyl: N,N-dimethylcarbamoyl and N,N-diethylcarbamoyl; for alkoxycarbonyl: methoxycarbonyl, ethoxycarbonyl and propoxycarbonyl; and for alkylenedioxy: methylenedioxy and ethylenedioxy.

A particular value for $R^6$ when it is non-toxic, biodegradable residue of a physiologically acceptable alcohol or phenol is, for example, a residue derived from a (1-6C)alkanol such as methanol or ethanol, or phenol, glycerol or the like.

A particular value for $R^7$ when it is alkyl is, for example, methyl, ethyl, propyl, isopropyl, butyl or pentyl; and when it is cycloalkyl is, for example, cyclobutyl, cyclopentyl or cyclohexyl.

Particular values for optional substituents which may be present on phenyl moieties include, by way of example, for halogeno, fluoro, chloro and bromo; for alkyl, methyl or ethyl; and for alkoxy, methoxy and ethoxy.

A specific value for X which is of particular interest is, for example, p-phenylene.

A preferred value for $R^6$ or $R^5$ is, for example, hydrogen and for $R^1$ is, for example, methyl, ethyl or propyl.

A preferred value for $R^3$ or $R^4$ is, for example, hydrogen, methyl, methoxy, ethoxy or isopropoxy.

A preferred value for $R^2$ is, for example, hydrogen.

A preferred value for Z is, for example, carboxy or 1H-tetrazol-5-yl, which latter is especially preferred and, in particular, when it is attached ortho to the group X.

It will be appreciated that the above definition of formula I compounds can readily be sub-divided, for example, into individual groups of compounds in which the pyridine moiety fused to ring B constitutes a pyrido-pyridine (that is a naphthyridine), pyrido-pyridazine, pyrido-pyrazine or pyrido-pyrimidine selected from those shown in the partial structural formulae IIa-IIj hereinafter, each of which constitutes a specific group of compounds of the invention.

A group of compounds of the invention which is of special interest comprises those compounds of the formula III wherein $R^1$, $R^2$, $R^3$, $R^4$, $R^5$, X and Z have any of the meanings defined above, and the physiologically acceptable salts thereof. Preferably, within this group, X is, for example, p-phenylene and Z is, for example, 1H-tetrazol-5-yl, and particularly when the groups X and Z are situated ortho to each other. It is especially preferred that one of $R^3$ and $R^4$ is selected from hydrogen, (1-4C)alkyl, (1-4C)alkoxy and fluoro(1-4C)alkoxy and is attached at the 6-position of the naphthyridine ring; and the other of $R^3$ and $R^4$ is hydrogen.

Compounds of the invention which are of particular interest include, for example, the compounds of formula I described hereinafter in the accompanying Examples. Of these, the compounds of formula I described in Examples 3, 4, 5, 6, 7 and 9 are of special interest and these compounds, or a physiologically acceptable salt thereof, are provided as a further feature of the invention.

Although all of the formula I compounds can form salts with suitable acids, it will be appreciated that the compounds of formula I wherein Z is other than an ester group or wherein $R^2$, $R^3$ or $R^4$ is a carboxy group can also form salts with bases as well as with acids. Particularly suitable salts for such compounds therefore include, for example, salts with bases affording physiologically acceptable cations, for example, alkali metal (such as sodium and potassium), alkaline earth metal (such as magnesium and calcium), aluminium and ammonium salts, as well as salts with suitable organic bases, such as with ethanolamine, methylamine, diethylamine or triethylamine, as well as salts with acids forming physiologically acceptable anions, such as salts with mineral acids, for example with hydrogen halides (such as hydrogen chloride and hydrogen bromide), sulphuric and phosphoric acid, and with organic acids, for example with p-toluenesulphonic, methanesulphonic, citric, tartaric and oxalic acids.

The compounds of formula I may be obtained by standard procedures of organic chemistry well known in the art for the production of structurally analogous compounds. Such procedures are provided as a further feature of the invention and include, by way of example, the following procedures in which the generic radicals have any of the values given above, unless stated otherwise:

a) For those compounds in which Z is carboxy (that is in which Z is a group of the formula —CO.OR$^6$ in which $R^6$ is hydrogen), a carboxylic acid derivative of the formula IV, in which Q is a protected carboxy group selected from (1-4C)alkoxycarbonyl (especially methoxy-, ethoxy-, propoxy- or t-butoxy-carbonyl), phenoxycarbonyl, benzyloxycarbonyl and carbamoyl, is converted to carboxy.

The conversion may be carried out, for example by hydrolysis, conveniently in the presence of a suitable base such as an alkali metal hydroxide, for example, lithium, sodium or potassium hydroxide. The hydrolysis is generally carried out in the presence of a suitable aqueous solvent or diluent, for example in an aqueous (1-4C)alkanol, such as aqueous methanol or ethanol. However, it may also be performed in a mixture of an aqueous and non-aqueous solvent such as water and toluene using a conventional quaternary ammonium phase transfer catalyst. The hydrolysis is generally performed at a temperature in the range, for example, 0°-120° C. depending on the reactivity of the group Q. In general, when Q is carbamoyl, temperatures in the range, for example, 40°-120° C. are required to effect the hydrolysis.

Alternatively, when Q is benzyloxycarbonyl, the conversion may also be performed by hydrogenolysis, for example using hydrogen at 1-3 bar in the presence of a suitable catalyst, such as palladium on charcoal or on calcium sulphate, in a suitable solvent or diluent such as an (1-4C)alkanol (typically ethanol or 2-propanol) and at a temperature in the range, for example, 0°-40° C.

Further, when Q is t-butoxycarbonyl, the conversion may also be carried out by hydrolysis at a temperature in the range, for example, 0°-100° C., in the presence of a strong acid catalyst, such as trifluoroacetic acid. The hydrolysis may either be performed in an excess of the acid or in the presence of a suitable diluent such as tetrahydrofuran, t-butyl methyl ether or 1,2-dimethoxyethane.

b) For those compounds of formula I wherein Z is tetrazolyl, a compound of the formula V in which L is a suitable protecting group, such as trityl, benzhydryl, trialkyl tin (for example trimethyltin) or triphenyltin, affixed to a nitrogen of the tetrazolyl moiety, is deprotected.

The reaction conditions used to carry out the deprotection necessarily depend on the nature of the group L. As an illustration, when it is trityl, benzhydryl, trialkyl tin or triphenyltin, the decomposition conditions include, for example, acid catalysed hydrolysis in a mineral acid (such as aqueous hydrochloric acid), conveniently in an aqueous solvent (such as aqueous dioxan or 2-propanol). Alternatively, a trityl or benzhydryl group may be removed by hydrogenolysis, for example as described in (a) above for conversion of a benzyloxycarbonyl to a carboxy.

Compounds of the formula V wherein L is trialkyltin or triphenyltin may be obtained, for example, by reaction of a nitrile of the formula XIV with a trialkyltin azide or triphenyltin azide respectively. The reaction is conveniently carried out in a suitable solvent or diluent, such as toluene or xylene, and at a temperature in the range, for example, 50°-150° C. The nitriles of the formula XIV may be obtained, for example, by reaction of a compound of the formula IX wherein $Y^1$ is a suitable leaving group, such as chloro, bromo, iodo, methanesulphonyloxy or p-toluenesulphonyloxy, with an alcohol of the formula XIII, using similar conditions to those used in process (d) described hereinafter. Alternatively, the nitriles of the formula XIV may be obtained from stepwise conversion of a compound of formula I wherein Z is a group of the formula —$CO.OR^6$ under standard conditions. The alcohols of formula XIII may be obtained, for example, by standard procedures such as that illustrated in Scheme 1 for compounds in which X is phenylene. The nitriles of the formula XIV may also be obtained, for example, by bromination of a suitably substituted 4'-methyl-biphenylcarbonitrile to the corresponding bromomethyl derivative followed by alkylation of an azaquinolone of formula VI in a similar manner to that described in process (c) described hereinafter.

Alternatively, compounds of the formula V may be obtained, for example, by reaction of an azaquinoline of the formula IX wherein $Y^1$ is a suitable leaving group (such as chloro, bromo, iodo, methanesulphonyloxy or p-toluenesulphonyloxy) with an alcohol of the formula XII under similar conditions to those described in process (d) hereinafter. The alcohols of formula XII may be obtained, for example, from the appropriate bromomethyl compound by standard procedures such as those shown in Scheme 1. It will be appreciated that other well known reagents and conditions may be used for carrying out the steps of Scheme 1 and may be dependent on the nature of the protecting group present on the tetrazole ring. For example, conventional hydrolytic conditions may be used for step (f) of Scheme 1 instead of reductive conditions.

c) An azaquinolone of the formula VI in which $R^1$ is other than hydrogen is alkylated with a compound of the formula VII wherein Hal. stands for a suitable leaving group such as chloro, bromo, iodo, methanesulphonyloxy or p-toluenesulphonyloxy.

The reaction is generally carried out in the presence of a suitable base, for example, an alkali metal alkoxide such as sodium methoxide or sodium ethoxide or an alkali metal hydride such as sodium hydride or an organic base such as diisopropylethylamine and in a suitable solvent or diluent, for example, a (1-4C)alkanol such as methanol or ethanol when an alkali metal alkoxide is used, or in a polar solvent such as N,N-dimethylformamide and at a temperature in the range, for example, 10°-100° C. Alternatively, a quaternary ammonium hydroxide may be used in a mixture of an aqueous and non-aqueous solvent such as water and dichloromethane. In carrying out process (c), when in the starting material Z is an acidic group, about two molecular equivalents of a suitable base is generally required, whereas when Z is a non-acidic group the presence of one molecular equivalent of a suitable base is generally sufficient.

Procedure (c) is particularly suitable for the production of those compounds of the formula I in which Z is a group of the formula —$CO.OR^6$ in which $R^6$ is other than hydrogen, for example wherein $R^6$ is (1-6C)alkyl, benzyl or phenyl, which compounds are also starting materials of formula IV for the reaction described in (a) above. Similarly, using an analogous procedure, but starting with the appropriate halomethyl tetrazolyl derivative of the formula VIII, the starting materials of the formula V may be obtained for procedure (b).

Certain of the azaquinolones of formula VI are already known and the remainder can in general be made by analogy therewith using standard procedures of organic chemistry well known in the art, for example as described in standard works of heterocyclic chemistry such as that edited by Elderfield or as described in *J. Med. Chem.* 1971, 14, 638. Alternatively, they may be obtained, for example, using a procedure such as that illustrated in Scheme 2. The necessary compounds of the formula VII (and also of formula VIII) may be made by standard procedures such as those which are illustrated in Scheme 1 for compounds in which X is phenylene.

Compounds of the formula VIII wherein X is phenylene may also be conveniently obtained by reaction of a Grignard reagent, formed from a suitably substituted 4-bromotoluene, with a trialkyltin halide, such as tributyltin chloride, followed by reaction of the resulting (substituted)phenyltrialkyltin compound with a bromobenzonitrile in the presence of a palladium(O) catalyst, such as tetrakis(triphenylphosphine)palladium, and azo(bisisobutyronitrile). The resultant substituted 4'-methyl-biphenylcarbonitrile may then be converted to a compound of the formula VIII by carrying out steps (b), (c) and (d) in a similar manner to that shown in Scheme 1. Alternatively, suitably substituted 4'-methyl-biphenylcarbonitriles may be obtained by reaction of 4-methylphenylboronic acid with an appropriately substituted bromobenzonitrile in the presence of a suitable palladium catalyst, such as palladium (II)chloride or tetrakis(triphenylphosphine)palladium, and azo(-bisisobutyronitrile).

(d) A compound of the formula IX wherein $Y^1$ is a suitable leaving group (such as chloro, bromo, iodo, methanesulphonyloxy or p-toluenesulphonyloxy) is reacted with an alcohol of the formula XI.

The reaction is generally carried out in the presence of a suitable base, for example an alkali metal alkoxide such as sodium methoxide or ethoxide or an alkali metal hydride such as sodium hydride and in a suitable solvent or diluent, for example a (1-4C)alkanol such as methanol or ethanol when an alkali metal alkoxide is used, or a polar solvent such as N,N-dimethylformamide. Alternatively, an alcohol of the formula XI may be used in the form of its preformed alkali metal salt (when Z is a non-acidic group) or di-alkali metal salt (when Z is an acidic group). The reaction is usually performed at a temperature in the range of 40° to 120° C. The reaction may in preference be carried out with a formula XI compound in the presence of an acid catalyst such as p-toluenesulphonic acid, instead of under basic conditions, and in the presence of an inert solvent or diluent such as toluene.

The compounds of the formula IX may be obtained, for example, by halogenation of the corresponding azaquinolone derivative of formula VI, for example, by reaction with phosphorus oxychloride in the absence of a solvent, or in the presence of an inert solvent or diluent such as toluene or dioxane, and at a temperature in the range 60°–110° C. The alcohols of the formula XI are known or can be prepared by standard procedures well known in the art.

Whereafter, those compounds of formula I wherein Z is 1H-tetrazol-5-yl may be obtained by stepwise conversion of a compound of the formula I wherein Z is a group of the formula —CO.OR$^6$ into the corresponding nitrile under standard conditions, followed by reaction of the nitrile with an azide such as an alkali metal azide, preferably in the presence of an ammonium halide, and preferably in the presence of a suitable polar solvent such as N,N-dimethylformamide and at a temperature in the range, for example, 50° to 160° C.

Whereafter, those compounds of the formula I wherein Z is —CO.NH.(1H-tetrazol-5-yl), a group of the formula —CO.NH.SO$_2$R$^7$ or a group of the formula —CO.OR$^6$ in which R$^6$ is other than hydrogen, may be obtained, for example, by reacting a carboxylic acid of the formula I in which Z is carboxy (or a reactive derivative of said acid) with 5-aminotetrazole, a sulphonamide of the formula NH$_2$.SO$_2$R$^7$ or a salt thereof (for example, an alkali metal salt), or a hydroxy compound of the formula HO.R$^6$ or with a salt thereof (for example, an alkali metal thereof). Suitable reactive derivatives include, for example the chloride, bromide, azide, anhydride and mixed anhydride with formic or acetic acid of the carboxylic acid of formula I as defined above. When the free acid form is used, the reaction is generally carried out in the presence of a suitable dehydrating agent such as dicyclohexylcarbodiimide or 3-(3-dimethylaminopropyl)-1-ethylcarbodiimide in the presence of a base such as triethylamine or pyridine. When a reactive derivative is used, either the reaction is carried out in the presence of a base such as mentioned above, or, for the preparation of a compound of the formula I wherein Z is a group of the formula —CO.NH.SO$_2$R$^7$ or a group of the formula —CO.OR$^6$, the sulphonamide or hydroxy compound is used in the form of a salt, such as its alkali metal salt (in particular the lithium, sodium or potassium salt thereof). The reaction is generally performed in the presence of a suitable diluent or solvent such as dioxan, t-butyl methyl ether or tetrahydrofuran and at a temperature in the range, for example, 0°–60° C.

Whereafter, when a salt of a compound of formula I is required, it may be obtained, for example, by reaction with the appropriate base affording a physiologically acceptable cation, or with the appropriate acid affording a physiologically acceptable anion, or by any other conventional salt formation procedure.

Further, when an optically active form of a compound of formula I is required, one of the aforesaid processes may be carried out using an optically active starting material. Alternatively, the racemic form of a compound of formula I in which Z is an acidic group may be resolved, for example by reaction with an optically active form of a suitable organic base, for example, ephedrine, N,N,N-trimethyl-(1-phenylethyl)ammonium hydroxide or 1-phenylethylamine, followed by conventional separation of the diastereoisomeric mixture of salts thus obtained, for example by fractional crystallisation from a suitable solvent, for example a (1-4C)alkanol, whereafter the optically active form of said compound of formula I may be liberated by treatment with acid using a conventional procedure, for example using an aqueous mineral acid such as dilute hydrochloric acid.

Certain of the intermediates defined herein are novel, for example the compounds of the formula IV, V and VI, and are provided as a further feature of the invention.

As started above, the compounds of formula I will have beneficial pharmacological effects in warm-blooded animals (including man) in diseases and medical conditions where amelioration of the vasoconstrictor and fluid retaining properties of the renin-angiotensin-aldosterone system is desirable, at least in part by antagonism of one or more of the physiological actions of AII. The compounds of the invention will thus be useful in the treatment of diseases or medical conditions such as hypertension, congestive heart failure and/or hyperaldosteronism in warm-blooded animals (including man), as well as in other diseases or medical conditions in which the renin-angiotensin-aldosterone system plays a significant causative role.

The antagonism of one or more of the physiological actions of AII and, in particular, the antagonism of the interaction of AII with the receptors which mediate its effects on a target tissue, may be assessed using one or more of the following, routine laboratory procedures.

Test A:

This in vitro procedure involves the incubation of the test compound initially at a concentration of 100 micromolar (or less) in a buffered mixture containing fixed concentrations of radiolabelled AII and a cell surface membrane fraction prepared from a suitable angiotensin target tissue. In this test, the source of cell surface membranes is the guinea pig adrenal gland which is well known to respond to AII. Interaction of the radiolabelled AII with its receptors (assessed as radiolabel bound to the particulate membrane fraction following removal of unbound radiolabel by a rapid filtration procedure such as is standard in such studies) is antagonized by compounds which also bind to the membrane receptor sites and the degree of antagonism (observed in the test as displacement of membrane-bound radioactivity) is determined readily by comparing the receptor-bound radioactivity in the presence of the test compound at the specified test concentration with a control value determined in the absence of the test compound. Using this procedure compounds showing at least 50% displacement of radiolabelled AII binding at a concentration of 10$^{-4}$ M are retested at lower concentrations to determine their potency. For determination of the IC$_{50}$ (concentration for 50% displacement of radiolabelled AII binding), concentrations of the test compound are ordinarily chosen to allow testing over at least four orders of magnitude centred about the predicted approximate IC$_{50}$, which latter is subsequently determined from a plot of percentage displacement against concentration of the test compound.

In general, acidic compounds of formula I as defined above show significant inhibition in Test A at a concentration of 50 micromolar or much less.

Test B

This in vitro test involves the measurement of the antagonistic effects of the test compound against AII-induced contractions of isolated rabbit aorta, maintained in a physiological salt solution at 37° C. In order to ensure that the effect of the compound is specific to antagonism of AII, the effect of the test compound on noradrenaline-induced contractions may also be determined in the same preparation.

In general, compounds of formula I as defined above wherein Z is an acidic group show significant inhibition in Test B at a final concentration of 50 micromolar or much less. [Note: Compounds of formula I wherein Z is a group of the formula —$CO.OR^6$ in which $R^6$ is other than hydrogen in general show only weak activity in the in vitro Test A or B.]

Test C

This in vivo test involves using terminally-anaesthetised or conscious rats in which an arterial catheter has been implanted under anaesthesia for the measurement of changes in blood pressure. The AII antagonistic effects of the test compound following oral or parenteral administration, are assessed against pressor responses induced by AII. To ensure that the effect is specific the effect of the test compound on vasopressin-induced pressor responses may also be determined in the same preparation.

The compounds of formula I generally show specific AII-antagonist properties in Test C at a dose of 50 mg/kg body weight or much less, without any overt toxicological or other untoward pharmacological effect.

Test D

This in vivo test involves the stimulation of endogenous AII biosynthesis in a variety of species including rat, marmoset and dog by introducing a diet of low sodium content and giving appropriate daily doses of a saluretic known as frusemide. The test compound is then administered orally or parenterally to the animal in which an arterial catheter has been inplanted under anasthesia for the measurement of changes in blood pressure.

In general compounds of formula I will show AII-antagonist properties in Test D as demonstrated by a significant reduction in blood pressure at a dose of 50 mg/kg body weight or much less, without any overt toxicological or other untoward pharmacological effect.

By way of illustration of the angiotensin II inhibitory properties of compounds of the formula I, the compound of Example 4 gave the following results in tests A and C described above:

In test A: an $IC_{50}$ of $2 \times 10^{-8}$M;

In test C: an $ED_{50}$ of 0.6 mg/kg (i.v. administration).

The compounds of formula I will generally be administered for therapeutic or prophylactic purposes to warm-blooded animals (including man) requiring such treatment in the form of a pharmaceutical composition, as is well known in the pharmaceutical art. According to a further feature of the invention there is provided a pharmaceutical composition comprising a compound of formula I or a salt thereof as defined above, together with a pharmaceutically acceptable diluent or carrier. Such compositions will conveniently be in a form suitable for oral administration (e.g. as a tablet, capsule, solution, suspension or emulsion) or parenteral administration (e.g. as an injectable aqueous or oily solution, or injectable emulsion).

The compounds of formula I may also be advantageously administered for therapeutic or prophylactic purposes together with another pharmacological agent known in the general art to be of value in treating one or more of the diseases or medical conditions referred to hereinabove.

In general a compound of formula I (or a pharmaceutically acceptable salt thereof as appropriate) will generally be administered to man so that, for example, a daily oral dose of up to 50 mg/kg body weight (and preferably of up to 10 mg/kg) or a daily parenteral dose of up to 5 mg/kg body weight (and preferably of up to 1 mg/kg) is received, given in divided doses as necessary, the precise amount of compound (or salt) administered and the route and form of administration depending on size, age and sex of the person being treated and on the particular disease or medical condition being treated according to principles well known in the medical arts.

In addition to their aforesaid use in therapeutic medicine in humans, the compounds of formula I are also useful in the veterinary treatment of similar conditions affecting commercially valuable warm-blooded animals, such as dogs, cats, horses and cattle. In general for such treatment, the compounds of the formula I will generally be administered in an analogous amount and manner to those described above for administration to humans. The compounds of formula I are also of value as pharmacological tools in the development and standardisation of test systems for the evaluation of the effects of AII in laboratory animals such as cats, dogs, rabbits, monkeys, rats and mice, as part of the continuing search for new and improved therapeutic agents.

The invention will now be illustrated by the following non-limiting Examples in which, unless otherwise stated:

(i) concentrations and evaporations were carried out by rotary evaporation in vacuo;

(ii) operations were carried out at room temperature, that is in the range 18°-26° C.;

(iii) flash column chromatography was performed on Merck Kieselgel 60 (Art. no. 9385) obtained from E Merck, Darmstadt, Germany;

(iv) yields, where given, are intended for the assistance of the reader only and are not necessarily the maximum attainable by diligent process development;

(v) proton NMR spectra were normally determined at 200 MHz in $CDCl_3$ using tetramethylsilane (TMS) as an internal standard, and are expressed as chemical shifts (delta values) in parts per million relative to TMS using conventional abbreviations for designation of major peaks: s, singlet; m, multiplet; t, triplet; br, broad; d, doublet;

(vi) $^{13}C$ NMR spectra were normally determined at 100 MHz in $CDCl_3$ or $d_6$-dimethylsulphoxide ($d_6$-DMSO) using the solvent signal as internal standard, and are expressed as chemical shifts (delta values) in parts per million relative to TMS; and (vii) all end-products had satisfactory microanalyses.

EXAMPLE 1

2.5M Sodium hydroxide solution (0.6 ml) was added to a solution of methyl 4'-[2-(methyl-1,5-naphthyridin-4-yloxy)methyl]biphenyl-2-carboxylate (A1) (191 mg)

in ethanol (2 ml). The solution was heated under reflux for 2.5 hours and then volatile material was removed by evaporation. The residue was dissolved in water (10 ml) and the solution acidified to pH 4 with 1M aqueous citric acid. The precipitated solid was collected and dried under high vacuum to give 4'-[(2-methyl-1,5-naphthyridin-4-yloxy)methyl]biphenyl-2-carboxylic acid (118 mg), as a white powder, m.p. 213°–214° C.; NMR (d$_6$-DMSO): 2.7(s,3H), 5.4(s,2H), 7.3(s,1H), 7.4–7.8(complex m,9H), 8.2(dd,1H), 8.8(dd,1H); mass spectrum (negative fast atom bombardment (−ve FAB), DMSO/glycerol (GLY)): 369 (M−H)$^-$, 159; microanalysis found: C,73.6; H,5.0; N,7.1; $C_{23}H_{18}N_2O_3.0.25\ H_2O$ requires: C,73.7; H,4.9; N,7.5%.

The starting methyl ester (A1) was obtained as follows:

(1) A 1.6M solution of butyllithium in hexane (24.0 ml) was added dropwise to a stirred solution of 4-bromotoluene (6.0 g) in dry tetrahydrofuran (THF) (50 ml) at −78° C. under an atmosphere of argon. The temperature was maintained at −78° C. for 20 minutes and then a 1M solution of anhydrous zinc chloride in ether (38.6 ml) was added. The solution was kept at −78° C. for 15 minutes, and then tetrakis(triphenylphosphine)palladium (60 mg) in THF (5 ml) was added, followed by methyl 2-iodobenzoate (6.1 g) in THF (10 ml). The solution was allowed to reach ambient temperature over 1 hour, then heated under reflux for 5 hours. The solvent was removed by evaporation and the residue was dissolved in chloroform (150 ml). The solution was washed with a solution of ethylenediamine tetracetic acid (10 g) in water (100 ml) and the aqueous layer was re-extracted with chloroform (100 ml). The combined organic extracts were dried (MgSO$_4$) and the solvent removed by evaporation. The residue was purified by flash chromatography, eluting with ethyl acetate/hexane(1:9 v/v) to give methyl 4'methylbiphenyl-2-carboxylate (B1) as a colourless oil (4.4 g); NMR: 2.4(s,3H), 3.65(s,3H), 7.2(s,4H), 7.35(m,3H), 7.5(m,1H), 7.8(d,1H).

(ii) N-Bromosuccinimide (8.1 g) and azo(-bisisobutyronitrile) (130 mg) were added to a solution of compound (B1) (9.3 g) in carbon tetrachloride (300 ml). The mixture was heated under reflux for 4 hours and then cooled to ambient temperature. Insoluble material was removed by filtration and the filtrate concentrated. The residue was purified by flash chromatography, eluting with ethyl acetate/hexane (1:9 v/v) to give methyl 4'-(bromomethyl)biphenyl-2-carboxylate (C1) as a solid (10.9 g), m.p. 48°–50° C.; NMR: 3.65(s,3H), 4.55(s,2H), 7.25–7.60 (complex m,7H), 7.85(d,1H).

(iii) Ethyl-(Z)-3-(3-pyridylamino)-2-butenoate (8.0 g) (obtained as described in *J. Royal Netherlands Chem. Soc.*, 1976, 95, 220) was added to a refluxing eutectic mixture of 26.5% v/v diphenyl and 73.5% v/v diphenyl oxide (20 ml). The solution was heated under reflux for 1 hour and then cooled. The precipitated solid was collected, washed with hexane (20 ml) and ether (20 ml), and then purified by flash chromatography, eluting initially with methanol/dichloromethane (1:4 v/v). There was thus obtained 2-methyl-1,7-naphthyridin-4-(1H)-one (0.96 g), as an off-white powder, m.p. >250° C. (sublimes); NMR (d$_6$-DMSO): 2.4(s,3H), 6.2(s,1H), 8.1(d,1H), 8.45(d,1H), 9.0(s,1H). Further elution of the chromatography column with aqueous ammonia/methanol/dichloromethane (2:99:99 v/v) gave the required 2-methyl-1,5-naphthyridin-4(1H)-one (D1) (2.25 g), as an off-white powder, m.p. >280° C. (decomp.); NMR: 2.65(s,3H), 6.65(s,1H), 7.6(dd,1H), 8.4(dd,1H), 8.8(dd,1H).

(iv) Sodium hydride (60% dispersion in mineral oil; 80 mg) was added to a stirred suspension of the 1,5-naphthyridinone (D1) (320 mg) in N,N-dimethylformamide (DMF) (10 ml). The mixture was stirred until evolution of hydrogen had ceased and then a solution of the bromomethyl compound (C1) in DMF (2 ml) was added. Stirring was continued for 16 hours and then water (100 ml) was added. The mixture was extracted with ethyl acetate (3×25 ml) and the extracts were washed with water (25 ml), followed by saturated sodium chloride solution (25 ml) and dried (MgSO$_4$). The solvent was removed by evaporation and the residue purified by flash chromatography, eluting with methanol/dichloromethane (1:19 v/v) to give methyl 4'-[(2-methyl-1,5-naphthyridin-4-yloxy)methyl]biphenyl-2-carboxylate (A1) (244 mg), as an off-white powder, m.p. 132°–134° C. (from ethyl acetate/hexane); NMR (CDCl$_3$): 2.7(s,3H), 3.6(s,3H), 5.5(s,2H), 6.9(s,1H), 7.3–7.7 (complex m,3H), 7.85(d,1H), 8.3(dd,1H), 8.9(dd,1H); $^{13}$C NMR: (benzylic CH$_2$) 70.6 ppm.

EXAMPLE 2

Concentrated hydrochloric acid (1.75 ml) was added to a hot solution of 2-methyl-4-[(2'-(2-triphenylmethyl-2H-tetrazol-5-yl)biphenyl-4-yl)methyl]-1,5-naphthyridine (A2) (650 mg) in methanol/ethanol (7:13 v/v; 10 ml). The solution was cooled and left to stand for 1 hour. The precipitated solid was collected and recrystallised from methanol/ethyl acetate to give 2-methyl-4-[(2'-(1H-tetrazol-5-yl)biphenyl-4-yl)methoxy]-1,5-naphthyridine hydrochloride (234 mg), as a white solid m.p. 178°–180° C.; NMR(d$_6$-DMSO): 2.9(s,3H), 5.6(s,2H), 7.2(d,2H), 7.4–7.7 (complex m,6H), 7.8(s,1H), 8.05(dd,1H), 8.7(dd,1H), 9.1(dd,1H); mass spectrum (−ve FAB, DMSO/GLY) 393(M−H)$^-$; microanalysis found: C,63.3; H,4.6; N,19.2; Cl,7.3; $C_{23}H_{18}N_6O.HCl.0.5\ H_2O$ requires: C,62.8; H,4.6; N,19.1; Cl. 8.1%.

The starting material A2 was obtained as follows:

Sodium hydride (60% dispersion in mineral oil; 250 mg) was added to a stirred suspension of 2-methyl-1,5-naphthyridin-4(1H)-one (1.0 g) in DMF (30 ml). The mixture was stirred until evolution of hydrogen had ceased and then a solution of 5-[2-(4'-bromomethylbiphenyl]-2-triphenylmethyl-2H-tetrazole (3.83 g) (obtained as described in European patent application, publication number 291969) in DMF (10 ml) was added. Stirring was continued for 72 hours and then water (200 ml) was added. The mixture was extracted with ethyl acetate (3×100 ml) and the extracts were washed with water (100 ml), followed by saturated sodium chloride (100 ml) and dried (MgSO$_4$). The solvent was removed by evaporation and the residue purified by flash chromatography, eluting with ethyl acetate/dichloromethane (1:9 v/v changing gradually to 1:4) to give 2-methyl-4-[2'-(2-triphenylmethyl-2H-tetrazol-5-yl)biphenyl-4-yl)methyl]1,5-naphthyridine (A2) (730 mg), as a white solid, m.p. 176°–177° C.; NMR (d$_6$-DMSO): 2.6(s,3H), 5.3(s,2H), 6.9(m,6H), 7.15(d, 2H), 7.25–7.9 (complex m, 17H), 8.25(dd,1H), 8.85(dd,1H).

EXAMPLE 3

Using an analogous procedure to that described in Example 2, but starting from 2-ethyl-4-[2'-(2-triphenylmethyl-2H-tetrazol-5-yl)biphenyl-4-yl)methyl]-1,5-naphthyridine (A3), there was obtained 2-ethyl-4-[(2'-(1H-tetrazol-5-yl)biphenyl-4-yl)methoxy]-1,5-naphthyridine hydrochloride, as a white powder, in 35% yield; m.p. 168°–171° C.; NMR (d$_6$-DMSO): 1.45(t,3H), 3.2(q,2H), 5.6(s,2H), 7.2(d,2H), 7.5–7.75 (complex m,7H), 7.8(s, 1H), 8.05(dd, 1H), 8.7(dd,1H), 9.1(dd,1H); mass spectrum (−ve FAB, DMSO/GLY): 407 (M−H)$^-$, 234; microanalysis found: C,64.0; H,4.4; N,18.5; Cl,6.9; C$_{24}$H$_{20}$ON$_6$O.HCl. 0.5 H$_2$O requires: C,63.5; H,4.85; N,18.5; Cl. 7.8%.

The starting material (A3) was obtained as follows:

(i) A mixture of 3-aminopyridine (5.0 g), methylpropionylacetate (7.6 g) and p-toluenesulphonic acid (0.5 g) was stirred for 96 hours and then ether (100 ml) was added. The solution was washed with water (100 ml) and dried (MgSO$_4$). The solvent was removed by evaporation and the residue purified by flash chromatography, eluting with ethyl acetate to give methyl-(Z)-3-(3-pyridylamino)-2-pentenoate (B3) (2.8 g) as an oil; NMR (CDCl$_3$): 1.1(t,3H), 2.5(q,2H), 3.7(s,3H), 4.95(s,1H), 7.3(m,1H), 7.4(m,1H), 8.4(m,2H), 10.3(br,1H).

(ii) The ester (B3) (2.76 g) was added to a refluxing eutectic mixture of 26.5% v/v diphenyl and 73.5% v/v diphenyl oxide (7 ml). The solution was heated under reflux for 30 minutes, cooled and diluted with hexane (50 ml) to precipitate 2-ethyl-1,5-naphthyridin-4(1H)-one (C3) (569 mg), as a pale brown solid, m.p. 244°–245° C.; NMR (CD$_3$OD): 1.4(t,3H), 2.8(q,2H), 6.4(s,1H), 7.7(dd,1H), 8.0(dd,1H), 8.7(dd,1H).

(iii) Using an analogous procedure to that described in Example 2, but starting from 2-ethyl-1,5-naphthyridin-4(1H)-one (C3), there was obtained 2-ethyl-4-[2'-(2-triphenylmethyl-2H-tetrazol-5-yl)biphenyl-4-yl)methyl]-1,5-naphthyridine (A3), as a pale brown solid, in 50% yield; m.p. 179°–180° C.; NMR: 1.3(t,3H), 2.9(q,2H), 5.3(s,2H), 6.9(m,6H), 7.15(d,2H), 7.3–7.8 (complex m, 17H), 8.3(dd,1H), 8.8(dd,1H).

EXAMPLE 4

Concentrated hydrochloric acid (20 ml) was added to a hot solution of 2-ethyl-6-methoxy-4-[(2'-(2-triphenylmethyl-2H-tetrazol-5-yl)biphenyl-4-yl)methoxy]-1,5-naphthyridine (A4) (9.4 g) in methanol (30 ml). The solution was cooled and left to stand for 1 hour. The precipitated solid was collected by filtration and washed with ethyl acetate (2×100 ml) to give 2-ethyl-6-methoxy-4-[(2'-(1H-tetrazol-5-yl)-biphenyl-4-yl)methoxy]-1,5-naphthyridine hydrochloride (5.4 g), as a white solid, m.p. 181°–182° C.; NMR (d$_6$DMSO): 1.4 (t, 3H), 3.1 (q, 2H), 4.05 (s, 3H), 5.65 (s, 2H), 7.2 (d, 2H), 7.5–7.8 (complex m, 8H), 8.55 (d, 1H); $^{13}$C NMR: (benzylic CH$_2$) 71.8; mass spectrum (−ve FAB, DMSO/GLY): 437 (M−H)$^-$; microanalysis, found: C, 63.3; H, 5.0; N, 17.6; Cl, 7.3%; C$_{25}$H$_{22}$N$_6$O$_2$.HCl requires: C, 63.2; H, 4.9; N, 17.7; Cl, 7.5%.

The starting material (A4) was obtained as follows:

(i) A solution of 5-amino-2-methoxypyridine (50 g), methyl propionylacetate (57.3 g) and p-toluenesulphonic acid (0.5 g) in benzene (200 ml) was heated under reflux with azeotropic removal of water for 20 hours. Volatile material was removed by evaporation and the residue added to a refluxing eutectic mixture of 26.5% v/v diphenyl and 73.5% v/v diphenyl oxide (140 ml). The solution was heated under reflux for 1 hour, cooled and diluted with hexane (500 ml). The precipitated solid was filtered off and triturated with hot methanol (500 ml) to give 2-ethyl-6-methoxy-1,5-naphthyridine-4 (1H)-one (B4) (32.3 g), as a pale brown solid, m.p. 279°–281° C.; NMR (d$_6$-DMSO): 1.2 (t, 3H), 2.65 (q, 2H), 3.95 (s, 3H), 6.3 (br s, 1H), 7.15 (d, 1H), 7.95 (d, 1H).

(ii) Compound B4 (5.0 g) was added to a stirred suspension of sodium hydride (60% dispersion in mineral oil; 1.08 g) in DMF (50 ml). The mixture was stirred at 50° C. until evolution of hydrogen had ceased and then a slurry of 5-[(2-(4'-bromomethyl-biphenylyl)]-2-triphenylmethyl-2H-tetrazole (13.7 g) in DMF (20 ml) was added. Stirring was continued for 20 hours and then the mixture was added to water (400 ml). The precipitated solid was collected by filtration and purified by flash chromatography, eluting with ethanol/ethyl acetate (2:98 v/v), to give 2-ethyl-6-methoxy-4-[(2'-(2-triphenylmethyl-2H-tetrazol-5-yl)biphenyl-4-yl)methoxy]-1,5-naphthyridine (A4) (9.4 g) as an off-white solid, m.p. 145°–148° C. (after trituration with ether); NMR (d$_6$-DMSO): 1.3 (t, 3H), 2.85 (q, 2H), 3.95 (s, 3H), 5.4 (s, 2H), 6.8–6.95 (m, 6H), 7.1–7.8 (complex m, 19H), 8.15 (d, 1H).

EXAMPLES 5–11

Using an analogous procedure to that described in Example 4, but starting from the appropriate compound of formula V (L=triphenylmethyl), the following compounds of formula IIa or IIc were obtained in yields of 17–71%.

EXAMPLE 5

6-Ethoxy-2-ethyl-4-[(2'-(1H-tetrazol-5-yl)biphenyl-4-yl)methoxy]-1,5-naphthyridine hydrochloride, m.p. 189°–191° C.; NMR (d$_6$-DMSO): 1.4 (2×t, 6H), 3.15 (q, 2H), 4.5 (q, 2H), 5.15 (s, 2H), 7.2 (d, 2H), 7.5–7.75 (complex m, 8H), 8.6 (d, 1H); mass spectrum (−ve FAB, DMSO/GLY): 451 (M−H)$^-$; microanalysis, found: C, 63.3; H, 5.3; N, 17.1; Cl, 6.8%; C$_{26}$H$_{24}$N$_6$O$_2$.HCl.0.25 H$_2$O requires: C, 63.3; H, 5.2; N, 17.0, Cl, 7.2%;

EXAMPLE 6

2-Ethyl-6-isopropoxy-4-[(2'-(1H-tetrazol-5-yl)biphenyl-4-yl)methoxy]-1,5-naphthyridine hydrochloride, m.p. 172°–173° C.; NMR (d$_6$-DMSO): 1.4 (d+t, 9H), 3.1(q, 2H), 5.35–5.45 (m, 1H), 5.65 (s, 2H), 7.15 (d, 2H), 7.4–7.7 (complex m, 8H), 8.55 (d, 1H); $^{13}$C NMR: (benzylic CH$_2$) 71.2; mass spectrum (−ve FAB, DMSO/GLY): 465 (M−H)$^-$; microanalysis, found: C, 63.2; H, 5.8; N, 16.0; Cl, 6.4%; C$_{27}$H$_{26}$N$_6$O$_2$.HCl.C-H$_3$OH requires: C, 62.9; H, 5.8; N, 15.7; Cl, 6.6%;

EXAMPLE 7

2-Ethyl-6-(2,2,2-trifluoroethoxy)-4-[(2'-(1H-tetrazol-5-yl)biphenyl-4-yl)methoxy]-1,5-naphthyridine hydrochloride, m.p. 149°–150° C.; NMR (d$_6$-DMSO): 1.4 (t, 3H), 3.15 (q, 2H), 5.15 (q, 2H), 5.65 (s, 2H), 7.2 (d, 2H), 7.5–7.8 (complex m, 8H), 8.75 (d, 1H); mass spectrum (−ve FAB, DMSO/GLY): 505 (M−H)$^-$, 271, 234; microanalysis, found: C, 57.3; H, 4.4; N, 14.7; Cl, 5.8;

$C_{26}H_{22}F_3N_6O_2.HCl.0.35\ CH_3CO_2CH_2CH_3$ requires: C, 57.3; H, 4.4; N, 14.6; Cl, 6.2%;

EXAMPLE 8

6-Dimethylamino-2-ethyl-4-[(2'-(1H-tetrazol-5-yl)biphenyl-4-yl)methoxy]-1,5-naphthyridine hydrochloride, m.p. 194°–195° C.; NMR (d$_6$-DMSO): 1.4 (t, 3H), 3.05 (q, 2H), 3.2 (s, 6H), 5.6 (s, 2H), 7.2 (d, 2H), 7.45–7.7 (complex m, 8H), 8.3 (d, 1H); mass spectrum (+ve FAB, DMSO/ m-nitrobenzyl alcohol (NBA)): 452 (M+H)$^+$, 409; microanalysis, found: C, 63.5; H, 5.4; N, 20.1; Cl, 7.5; H$_2$O 0.4%; $C_{26}H_{25}N_7O.HCl.0.4$ H$_2$O requires: C, 63.8; H, 5.4; N, 20.0; Cl, 7.3; H$_2$O 0.4%;

EXAMPLE 9

2-Ethyl-6-methyl-4-[(2'-(1H-tetrazol-5-yl)biphenyl-4-yl)-methoxy]-1,5-naphthyridine hydrochloride, m.p. 193°–194° C.; NMR (d$_6$-DMSO): 1.4 (t, 3H), 2.7 (s, 3H), 3.2 (q, 2H), 5.6 (s, 2H), 7.2 (d, 2H), 7.5–7.6 (m, 4H), 7.65–7.75 (m, 2H), 7.8 (s, 1H), 7.9 (d, 1H), 8.65 (d, 1H); $^{13}$C NMR: (benzylic CH$_2$) 72.0; mass spectrum (−ve FAB, DMSO/GLY): 421 (M−H)$^-$, 311, 234; microanalysis, found: C, 65.4; H, 4.9; N, 18.3; Cl, 7.5%; $C_{25}H_{22}N_6O.HCl$ requires: C, 65.4; H, 5.1; N, 18.3; Cl, 7.7%;

EXAMPLE 10

2-Ethyl-8-methyl-4-[(2'-(1H-tetrazol-5-yl)biphenyl-4-yl)methoxy]-1,5-naphthyridine hydrochloride, m.p. 171°–174° C.; NMR (d$_6$-DMSO): 1.4 (t, 3H), 2.85 (s, 3H), 3.1 (q, 2H), 5.5 (s, 2H), 7.2 (d, 2H), 7.5–7.7 (complex m, 7H), 7.85 (d, 1H), 8.85 (d, 1H); mass spectrum (−ve FAB, DMSO/GLY): 421 (M−H)$^-$; microanalysis, found: C, 64.0; H, 5.0; N, 18.0%; $C_{25}H_{22}N_6O.HCl.$ 0.5H$_2$O requires: C, 64.2; H, 5.1; N, 18.0%;

EXAMPLE 11

2-Methyl-4-[(2'-(1H-tetrazol-5-yl)biphenyl-4-yl)methoxy]-1,7-naphthyridine hydrochloride, m.p. 154°–156° C.; NMR (d$_6$-DMSO): 3.1 (s, 3H), 5.55 (s, 2H), 7.25 (d, 2H), 7.4–7.8 (complex m, 7H), 8.2 (d, 1H), 8.8 (d, 1H), 10.0 (s, 1H); mass spectrum (−ve FAB, DMSO/GLY): 393 (M−H)$^-$, 234; microanalysis, found: C, 61.6; H, 4.6; N, 18.0; H$_2$O, 3.0%; $C_{23}H_{18}N_6O.HCl.0.75$ H$_2$O requires: C, 62.1; H, 4.6; N, 18.9; H$_2$O, 3.0%.

The necessary starting materials of formula V were obtained in yields of 54–83% using an analogous procedure to that described in Example 4, part (ii), but starting from the appropriate naphthyridinones of formula VI. The compounds of formula V had the following properties:

6-Ethoxy-2-ethyl-4-[(2'-(2-triphenylmethyl-2H-tetrazol-5-yl)biphenyl-4-yl)methoxy]-1,5-naphthyridine, m.p. 177°–178° C.; NMR (d$_6$-DMSO): 1.3–1.4 (2×t, 6H), 2.8 (q, 2H), 4.45 (q, 2H), 5.4 (s,2H), 6.8–6.9 (m, 6H), 7.1–7.7 (complex m, 18H), 7.8 (dd, 1H), 8.15 (d, 1H);

2-Ethyl-6-isopropoxy-4-[(2'-2-triphenylmethyl-2H-tetrazol-5-yl)biphenyl-4-yl)methoxy]-1,5-naphthyridine, m.p. 135°–136° C.; NMR (d$_6$-DMSO): 1.2 (d+t, 9H), 2.8 (q, 2H), 5.4 (s+q, 3H), 6.7–6.9 (m, 6H), 7.1–7.5 (complex m, 16H), 7.55–7.65 (m, 2H), 7.8 (dd, 1H), 8.1 (d, 1H);

2-Ethyl-6-(2,2,2-trifluoroethoxy)-4-[(2'-(2-triphenylmethyl-2H-tetrazol-5-yl)biphenyl-4-yl)methoxy]-1,5-naphthyridine, m.p. 159°–160° C.; NMR (d$_6$-DMSO): 1.35 (t, 3H), 2.9 (q, 2H), 4.9 (q, 2H), 5.25 (s, 2H), 6.85–7.0 (m, 7H), 7.15–7.6 (complex m, 17H), 7.95 (d, 1H), 8.25 (d, 1H); $^{13}$C NMR: (benzylic CH$_2$) 71.0;

6-Dimethylamino-2-ethyl-4-[(2'-(2-triphenylmethyl-2H-tetrazol-5-yl)biphenyl-4-yl)methoxy]-1,5-naphthyridine, m.p. 155°–156° C.; NMR (d$_6$-DMSO): 1.3 (t, 3H), 2.85 (q, 2H), 3.2 (s, 6H), 5.4 (s, 2H), 6.8–6.9 (m, 6H), 7.15–7.7 (complex m, 18H), 7.8 (dd, 1H), 8.0 (d, 1H);

2-Ethyl-6-methyl-4-[(2'-(2-triphenylmethyl-2H-tetrazol-5-yl)biphenyl-4-yl)methoxy]-1,5-naphthyridine, m.p. 193° C.; NMR (d$_6$-DMSO): 1.3 (t, 3H), 2.6 (s, 3H), 2.85 (q, 2H), 5.3 (s, 2H), 6.8–7.85 (complex m, 25H), 8.15 (d, 1H);

2-Ethyl-8-methyl-4-[(2'-(2-triphenylmethyl-2H-tetrazol-5-yl)biphenyl-4-yl)methoxy]-1,5-naphthyridine, m.p. 173°–175° C.; NMR (d$_6$-DMSO): 1.35 (t, 3H), 2.7 (s, 3H), 2.9 (q, 2H), 5.3 (s, 2H), 6.8–6.9 (m, 6H), 7.1–7.7 (complex m, 18H), 7.8 (d, 1H), 8.65 (d, 1H);

2-Methyl-4-[(2'-(2-triphenylmethyl-2H-tetrazol-5-yl)biphenyl-4-yl)methoxy]-1,7-naphthyridine, m.p. 156°–157° C.; NMR (d$_6$-DMSO): 2.6 (s, 3H), 5.35 (s, 2H), 6.8–6.9 (m, 7H), 7.15 (d, 2H), 7.3–7.7 (complex m, 14H), 7.75–7.9 (m, 2H), 8.4 (d, 1H), 9.2 (s, 1H).

The necessary starting materials of formula VI were obtained in yields of 5–60% using an analogous procedure to that described in Example 4 part (i), but starting from the appropriate 3-aminopyridine. The compounds of formula VI had the following properties:

6-Ethoxy-2-ethyl-1,5-naphthyridin-4(1H)-one, m.p. 248°–249° C.; NMR (d$_6$-DMSO): 1.3 (2×t, 6H), 2.65 (q, 2H), 4.4 (q, 2H), 6.2 (br s, 1H), 7.1 (d, 1H), 7.95 (d, 1H);

2-Ethyl-6-isopropoxy-1,5-naphthyridin-4-(1H)-one, m.p. 245°–246° C.; NMR (d$_6$-DMSO): 1.25 (t, 3H), 1.35 (d, 6H), 2.6 (q, 2H), 5.4 (m, 1H), 6.15 (br, s, 1H), 7.0 (d, 1H), 7.9 (d, 1H);

2-Ethyl-6-(2,2,2-trifluoroethoxy)-1,5-naphthyridin-4(1H)-one, m.p. 302°–306° C. (decomp); NMR (d$_6$-DMSO): 1.3 (t, 3H), 2.7 (q, 2H), 5.1 (q, 2H), 6.35 (s, 1H), 7.3 (d, 1H), 8.1 (d, 1H);

6-Dimethylamino-2-ethyl-1,5-naphthyridin-4(1H)-one, m.p. 307° C. (decomp); NMR (d$_6$-DMSO): 1.25 (t, 3H), 2.7 (q, 2H), 3.25 (s, 6H), 6.65 (s, 1H), 7.3 (d, 1H), 7.95 (d, 1H);

2-Ethyl-6-methyl-1,5-naphthyridin-4-(1H)-one, m.p. 255°–269° C. (decomp); NMR (d$_6$-DMSO): 1.3 (t, 3H), 2.65 (s, 3H), 2.7 (q, 2H), 6.35 (s, 1H), 7.35 (d, 1H), 7.95 (d, 1H);

2-Ethyl-8-methyl-1,5-naphthyridin-4(1H)-one, m.p. 239°–240° C.; NMR (d$_6$-DMSO): 1.3 (t, 3H), 2.65 (s, 3H), 2.8 (q, 2H), 6.4 (br s, 1H), 7.4 (d, 1H), 8.5 (d, 1H).

2-Methyl-1,7-naphthyridin-4-(1H)-one was obtained as described in Example 1, part (iii).

The 3-aminopyridines used in Examples 8, 9 and 10 were obtained as follows:

5-amino-2-methylpyridine was obtained as described in *Chem. Pharm. Bull. Japan*, 1987, 35 (10), 4101–9;

3-amino-4-methylpyridine was obtained as described in Roczniki Chem., 1956, 30, 475, 479 (*Chemical Abstracts*, 1957, 14722);

5-amino-2-dimethylaminopyridine was obtained as described in *Chem. Ber.*, 1928, 61, 427.

2-(2,2,2-trifluoroethoxy)-5-aminopyridine used in Example 7 was obtained as described in U.K. Patent Application No. 2029411. The 3-aminopyridines used in Examples 5 and 6 were made by an analogous process using the appropriate alkali metal alkoxide, and were used without purification or characterisation.

EXAMPLE 12

Using an analogous procedure to that described in Example 4, but starting from 2-ethyl-6-[2-(trimethylsilyl)ethoxy]-4-[2'-(2-triphenylmethyl-2H-tetrazol-5-yl)biphenyl-4-yl)methoxy]-1,5-naphthyridine (A12), there was obtained in 44% yield 2-ethyl-6-hydroxy-4-[(2'-(1H-tetrazol-5-yl)biphenyl-4-yl)methoxy]-1,5-naphthyridine hydrochloride, as a white powder, m.p. 200°-250° C. (slow decomposition); NMR (d$_6$-DMSO): 1.35(t,3H); 3.0(q,2H), 5.05(d,2H), 7.0(d,1H), 7.15(d,2H), 7.5-7.75 (complex m,7H), 8.3(d,1H); mass spectrum (+ve FAB, DMSO/NBA): 425 (M+H)$^+$; microanalysis, found: C,62.7; H,4.5; N,18.4; Cl,7.4%; C$_{24}$H$_{20}$N$_6$O$_2$.HCl requires: C,62.5; H,4.6; N,18.2; Cl,7.7%.

The starting material (A12) was obtained as follows:

(i) Potassium t-butoxide (25.8 g) was added portionwise over 20 minutes to a solution of 2-(trimethylsilyl)ethanol (20.8 g) and 2-chloro-5-nitropyridine (27.8 g) in DMF (170 ml). The mixture was stirred for 18 hours and then poured into ice-water (900 ml). The mixture was extracted with ethyl acetate (3×300 ml) and the extracts were washed with water (200 ml), followed by saturated sodium chloride solution (200 ml) and dried (MgSO$_4$). Volatile material was removed by evaporation to give 5-nitro-2-[2-(trimethylsilyl)ethoxy]pyridine (34.9 g) as an oil; NMR: 0.05(s,9H), 1.1-1.2(m,2H), 4.45-4.55(m,2H), 6.75(d,1H), 8.3(dd,1H), 9.05(d,1H).

(ii) 5-Nitro-2-[2-(trimethylsilyl)ethoxy]pyridine (36.8 g) was dissolved in ethanol (270 ml) and catalytically hydrogenated at atmospheric pressure over platinum oxide (300 mg). The catalyst was removed by filtration through diatomaceous earth. The solvent was removed by evaporation and the residue triturated with hexane to give 5-amino-2-[2-(trimethylsilyl)ethoxy]pyridine (20.0 g), as dark crystals, m.p. 59°-61° C.; NMR: 0.0(s,9H), 0.95-1.05(m,2H), 3.1-3.3(br s, 2H), 4.2-4.3(m,2H), 6.5(d,1H), 6.95(dd,1H), 7.6(d,1H).

(iii) Using an analogous procedure to that described in Example 4, part (i), but starting from 5-amino-2-[2-(trimethylsilyl)ethoxy]pyridine, there was obtained in 62% yield 2-ethyl-6-[2-(trimethylsilyl)ethoxy]-1,5-naphthyridin-4-(1H)-one, as a white solid, m.p. 193° C.; NMR: −0.1(s,9H), 0.85(t,2H), 1.3(t,3H), 2.8(q,2H), 4.1(t,2H), 6.55(s,1H), 6.9(d,1H), 8.2(d,1H).

(iv) Using an analogous procedure to that described in Example 4, part (ii), but starting from 2-ethyl-6-[2-(trimethylsilyl)ethoxy]-1,5-naphthyridin-4-(1H)-one, there was obtained in 75% yield 2-ethyl-6-[2-(trimethylsilyl)ethoxy]-4-[2'-triphenylmethyl-2H-tetrazol-5-yl)biphenyl-4-yl)methoxy]-1,5-naphthyridine (A12), as a white solid, m.p. 113°-115° C.; NMR: 0.05(s,9H), 1.1-1.2(m,2H), 1.35(t,3H), 2.9(q,2H), 4.55-4.65(m,2H), 5.2(s,2H), 6.8-7.5 (complex m,24H), 7.85-7.95(m,1H), 8.1(d,1H).

EXAMPLE 13

Using an analogous procedure to that described in Example 4, but starting from 6-chloro-2-ethyl-4-[(2'-(2-triphenylmethyl-2H-tetrazol-5-yl)biphenyl-4-yl)methoxy]-1,5-naphthyridine (A13), there was obtained in 82% yield 6-chloro-2-ethyl-4-[(2'-(1H-tetrazol-5-yl)biphenyl-4-yl)methoxy]-1,5-naphthyridine hydrochloride. m.p. 186°-187° C.; NMR (d$_6$-DMSO): 1.4(t,3H), 3.15(q,2H), 5.6(s,2H), 7.2(d,2H), 7.5-7.7 (complex m,6H), 7.8(s,1H), 8.1(d,1H), 8.8(d,1H); mass spectrum (+ve FAB, DMSO/GLY): 443 (M+H)$^+$; microanalysis, found: C,59.6; H,4.5; N,17.4; Cl,14.4; H$_2$O, 0.8%; C$_{24}$H$_{19}$ClN$_6$O.HCl.0.25.H$_2$O requires: C,59.6; H,4.2; N,17.4; Cl,14.7; H$_2$O, 0.9%.

The starting material (A13) was obtained as follows:

(i) Using an analogous procedure to that described in Example 4, part (i), but starting from 5-amino-2-chloropyridine, there was obtained in 13% yield 6-chloro-2-ethyl-1,5-naphthyridin-4(1H)-one, m.p. 269°-270° C.; NMR (d$_6$-DMSO): 1.25(t,3H), 2.65(q,2H), 6.2(s,1H), 7.7(d,1H), 8.0(d,1H).

(ii) Using an analogous procedure to that described in Example 4, part (ii), but starting from 6-chloro-2-ethyl-1,5-naphthyridin-4-(1H)-one, there was obtained in 86% yield 6-chloro-2-ethyl-4-[(2'-(2-triphenylmethyl-2H-tetraol-5-yl)biphenyl-4-yl)methoxy]-1,5-naphthyridine (A13), m.p. 192°-193° C.; NMR (d$_6$-DMSO): 1.3(t,3H), 2.9(q,2H), 5.4(s,2H), 6.8-6.9(m,6H), 7.3-7.7(complex m,15H), 7.75-7.85(m,2H), 8.3(d,1H).

EXAMPLE 14

Using an analogous procedure to that described in Example 4, but starting from 7-chloro-2-ethyl-6-isopropoxy-4-[(2'-(2-triphenylmethyl-2H-tetrazol-5-yl)biphenyl-4-yl)methoxy]-1,5-naphthyridine (A14), there was obtained in 79% yield 7-chloro-2-ethyl-6-isopropoxy-4-[(2'-(1H-tetrazol-5-yl)biphenyl-4-yl)methoxy]-1,5-naphthyridine hydrochloride as a solid, m.p. 197°-201° C.; NMR (d$_6$-DMSO): 1.4(t,3H), 1.5(d,6H), 3.1(q,2H), 5.35-5.45(m,1H), 5.65(s,2H), 7.2(d,2H), 7.4-7.7(complex m,7H), 8.8(s,1H); $^{13}$C NMR: (benzylic CH$_2$) 71.1; mass spectrum (+ve FAB, DMSO/NBA): 501 (M+H)$^+$; microanalysis, found: C,60.6; H,4.8; N,15.1%; C$_{26}$H$_{23}$ClN$_6$O$_2$.HCl requires: C,60.3; H,4.8; N,15.6%.

The starting material (A14) was obtained as follows:

(i) Using an analogous procedure to that described in Example 4, part (i), but starting from 5-amino-3-chloro-2-isopropoxypyridine (obtained as described in GB Patent Application No. 20011316A) there was obtained in 42% yield 7-chloro-2-ethyl-6-isopropoxy-1,5-naphthyridin-4(1H)-one, m.p. 231°-235° C.; NMR (d$_6$-DMSO+d$_4$-acetic acid): 1.2(t,3H), 1.4(d,6H), 2.7(q,2H), 5.55-5.65(m,1H), 6.5(s,1H), 8.1(s,1H).

(ii) Using an analogous procedure to that described in Example 4, part (ii), but starting from 7-chloro-2-ethyl-6-isopropoxy-1,5-naphthyridin-4(1H)-one, there was obtained in 69% yield 7-chloro-2-ethyl-6-isopropoxy-4-[(2'-(2-triphenylmethyl-2H-tetrazol-5-yl)biphenyl-4-yl)methoxy]-1,5-naphthyridine (A14), m.p. 179°-183° C.; NMR: 1.3(t,3H), 1.4(d,6H), 2.4(q,2H), 5.2(s,2H), 5.55-5.65(m,1H), 6.6(s,1H), 6.8-7.0(m,6H), 7.1-7.6(complex m,16H), 8.0(s,1H), 8.2(s,1H).

EXAMPLE 15

Pharmaceutical dosage forms, suitable for presenting the compounds of the invention for therapeutic or prophylactic use, include conventional tablet, capsule, injection and aerosol formulations. The following illustrative formulations may be obtained by conventional procedures well known in the art of pharmacy and are suitable for therapeutic or prophylactic use in humans:

| Tablet I | mg/tablet |
|---|---|
| Compound Z* | 5.0 |
| Lactose Ph. Eur. | 89.25 |
| Croscarmellose sodium | 4.0 |
| Maize starch paste (5% w/v aqueous paste) | 0.75 |
| Magnesium stearate | 1.0 |

| Tablet II | mg/tablet |
|---|---|
| Compound Z* | 50 |
| Lactose Ph. Eur. | 223.75 |
| Croscarmellose sodium | 6.0 |
| Maize starch | 15.0 |
| Polyvinylpyrrolidone (5% w/v aqueous paste) | 2.25 |
| Magnesium stearate | 3.0 |

| Tablet III | mg/tablet |
|---|---|
| Compound Z* | 100 |
| Lactose Ph. Eur. | 182.75 |
| Croscarmellose sodium | 12.0 |
| Maize starch paste (5% w/v aqueous paste) | 2.25 |
| Magnesium stearate | 3.0 |

| Capsule | mg/capsule |
|---|---|
| Compound Z* | 10 |
| Lactose Ph. Eur. | 488.5 |
| Magnesium stearate | 1.5 |

Note
compound Z* may be a compound of formula I such as one of the previously described specific examples herein or a physiologically acceptable salt thereof

CHEMICAL FORMULAE

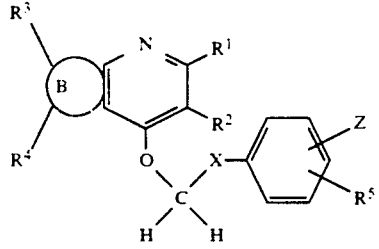

I

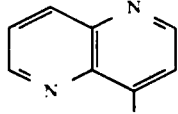

IIa

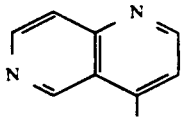

IIb

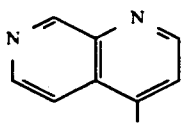

IIc

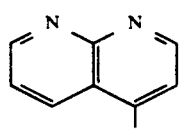

IId

-continued
CHEMICAL FORMULAE

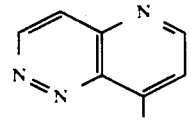

IIe

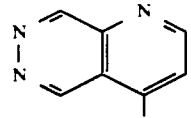

IIf

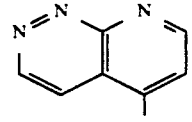

IIg

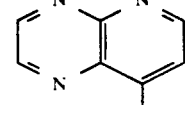

IIh

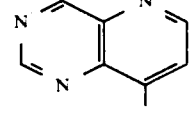

IIi

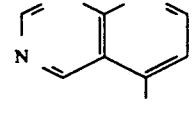

IIj

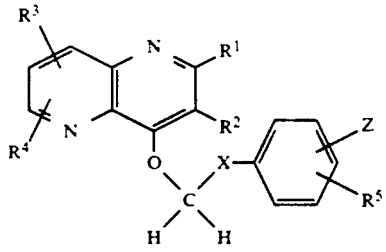

III

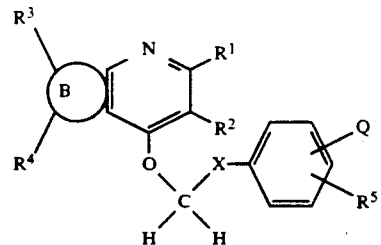

IV

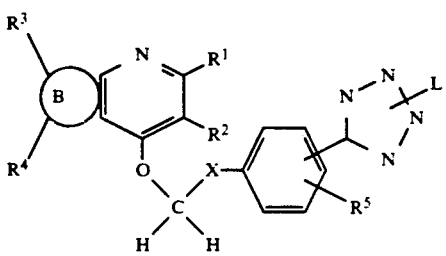

V

21
-continued
CHEMICAL FORMULAE
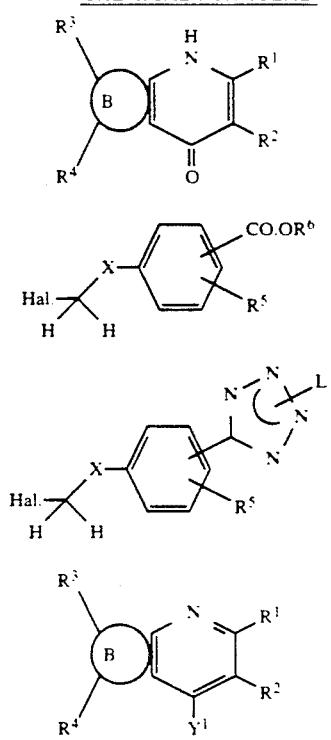
22
-continued
CHEMICAL FORMULAE
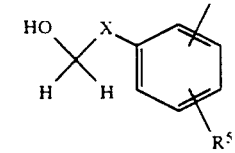     XI
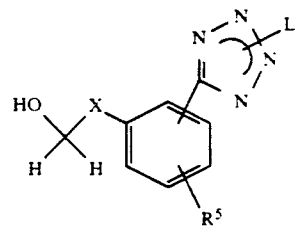     XII
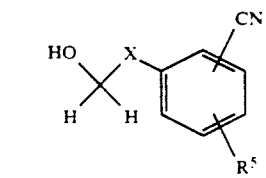     XIII
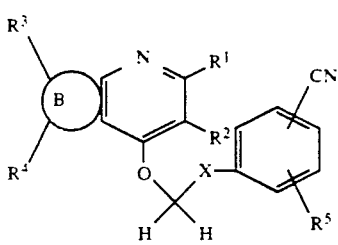     XIV
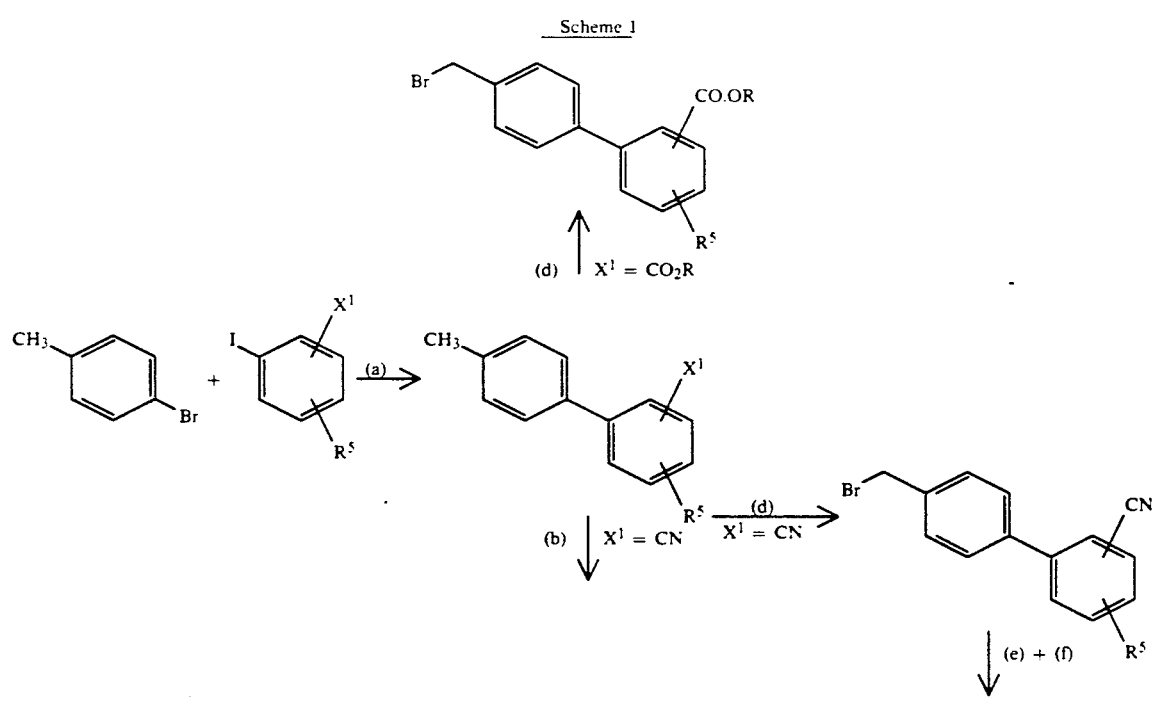

-continued
Scheme 1
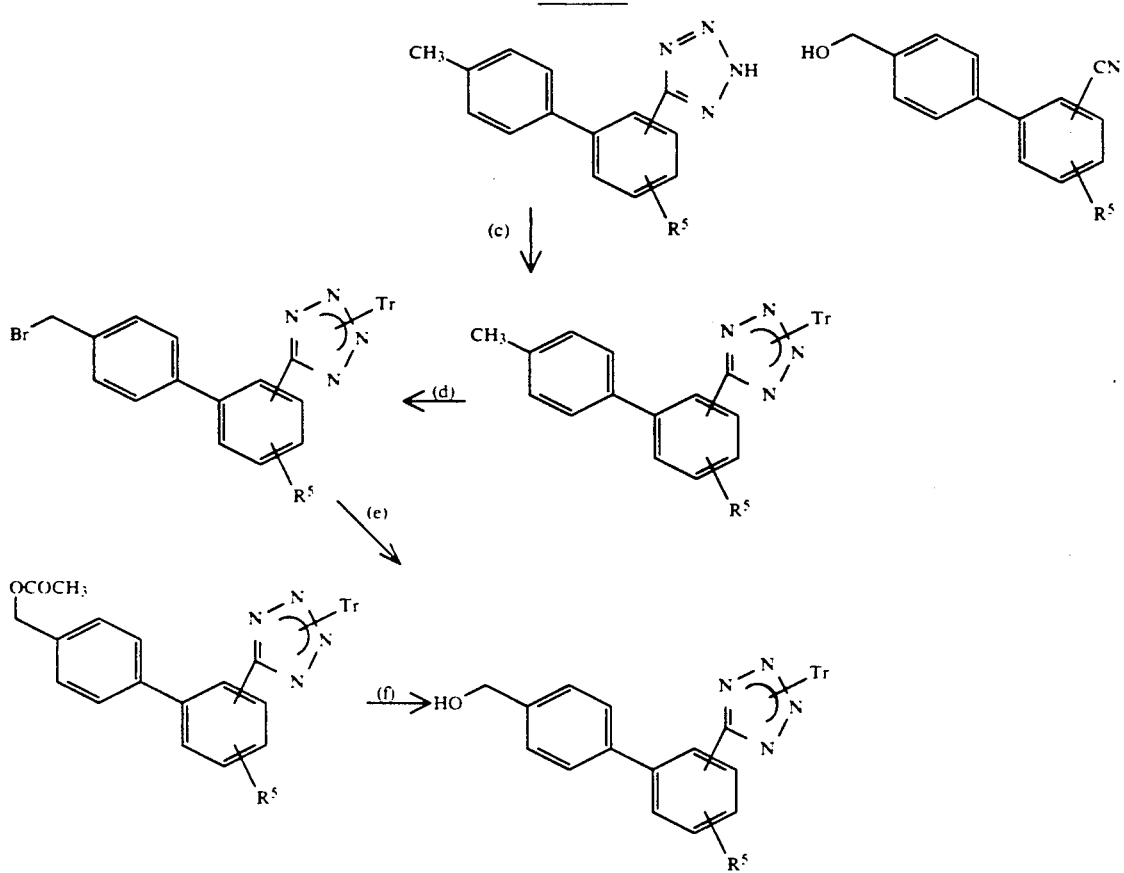
Note
R = lower alkyl, benzyl, phenyl.
Tr = triphenylmethyl(trityl)
Reagents
a) BuLi/THF, ZnCl₂/Et₂O, Pd(Ph₃P)₄
b) Bu₃Sn N₃/toluene. HCl/toluene
c) Tr Cl/Et₃N/CH₂Cl₂
d) N-bromosuccinimide/azoisobutyronitrile/CCl₄
e) Potassium acetate, hexaoxacyclooctadecane, DME, reflux
f) Lithium borohydride, THF, 0-25° C.
Scheme 2
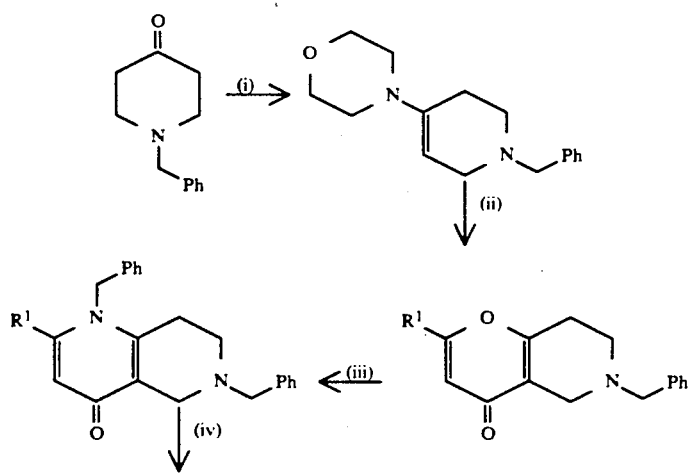

Scheme 2

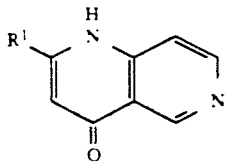

Reagents
a) morpholine, toluene, reflux, 16 hours
b) R¹.CO.CH₂.CO₂R (e.g. CH₃CH₂.CO.CH₂.CO₂.CH₃), xylene, reflux (Dean and Stark apparatus) [R = lower alkyl]
c) benzylamine, 140°C (Dean and Stark apparatus), 24 hours, conc HCl (catalyst)
d) palladium on carbon, xylene, reflux, 96 hours

What we claim is:

1. An azaquinoline derivative of the formula I

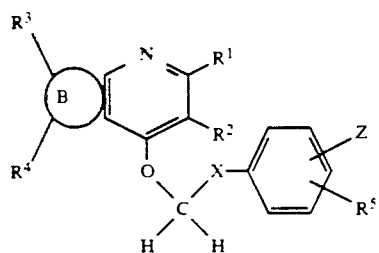

I wherein ring B is a pyridine, pyridazine, pyrimidine or pyrazine moiety; $R^1$ is hydrogen, (1-8C)alkyl, (3-8C)cycloalkyl, (3-8C)cycloalkyl-(1-4C)alkyl, phenyl, phenyl(1-4C)alkyl or (1-4C)alkyl bearing one or more fluoro substituents; $R^2$ is hydrogen, (1-8C)alkyl, (3-8C)cycloalkyl, (3-8C)cycloalkyl-(1-4C)alkyl, carboxy, (1-4C)alkoxycarbonyl, cyano, nitro, phenyl or phenyl(-1-4C)alkyl; $R^3$ and $R^4$ are independently selected from hydrogen, (1-4C)alkyl, (1-4C)alkoxy, fluoro(1-4C)alkoxy, halogeno, trifluoromethyl, cyano, nitro, hydroxy, amino, alkylamino and dialkylamino of up to 6 carbon atoms, carboxy, (1-4C)alkoxycarbonyl, carbamoyl and N-alkylcarbamoyl and di-(N-alkyl)carbamoyl of up to 7 carbon atoms; or when ring B is a pyridine moiety, $R^3$ and $R^4$ may optionally together form a (1-4C)alkylenedioxy group; $R^5$ is hydrogen, (1-4C)alkyl, (1-4C)alkoxy, halogeno, trifluoromethyl, cyano or nitro; X is phenylene optionally bearing a substituent selected from (1-4C)alkyl, (1-4C)alkoxy, halogeno, trifluoromethyl, cyano and nitro, or X is a direct bond between the adjacent phenyl and methylene groups; Z is 1H-tetrazol-5-yl, —CO.NH.(1H-tetrazol-5-yl) or a group of the formula —CO.OR⁶ or —CO.NH.SO₂.R⁷ in which R⁶ is hydrogen or a non-toxic, biodegradable residue of a physiologically acceptable alcohol or phenol, and $R^7$ is (1-6C)alkyl, (3-8C)cycloalkyl or phenyl; and wherein any of said phenyl moieties may be unsubstituted or bear one or two substituents independently selected from (1-4C)alkyl, (1-4C)alkoxy, halogeno, cyano and trifluoromethyl; or a physiologically acceptable salt thereof.

2. A compound as claimed in claim 1 wherein $R^1$ is hydrogen, methyl, ethyl, propyl, butyl, isobutyl, sec-butyl, pentyl, hexyl, cyclopropyl, cyclopentyl, cyclohexyl, cyclopropylmethyl, cyclopentylmethyl, cyclohexylmethyl, 2-cyclopentyl-ethyl, phenyl, benzyl, 1-phenylethyl, 2-phenylethyl, fluoromethyl, trifluoromethyl, 2,2,2-trifluoroethyl or pentafluoroethyl; $R^2$ is hydrogen, methyl, ethyl, propyl, butyl, isobutyl, sec-butyl, pentyl, hexyl, cyclopropyl, cyclopentyl, cyclohexyl, cyclopropylmethyl, cyclopentylmethyl, cyclohexylmethyl, 2-cyclopentyl-ethyl, carboxy, methoxycarbonyl, ethoxycarbonyl, propoxycarbonyl, cyano, nitro, phenyl, benzyl, 1-phenylethyl or 2-phenylethyl; $R^3$ and $R^4$ are independently selected from hydrogen, methyl, ethyl, methoxy, ethoxy, isopropoxy, trifluoromethoxy, 2-fluoroethoxy, 2,2,2-trifluoroethoxy, 3,3,3-trifluoropropoxy, fluoro, chloro, bromo, iodo, trifluoromethyl, cyano, nitro, hydroxy, amino, methylamino, ethylamino, butylamino, dimethylamino, diethylamino, dipropylamino, carboxy, methoxycarbonyl, ethoxycarbonyl, propoxycarbonyl, carbamoyl, N-methylcarbamoyl, N-ethylcarbamoyl, N,N-dimethylcarbamoyl, N,N-diethylcarbamoyl; or when ring B is a pyridine moiety, $R^3$ and $R^4$ may optionally together form a methylenedioxy and ethylenedioxy group; $R^5$ is hydrogen, methyl, ethyl, methoxy, ethoxy, isopropoxy, fluoro, chloro, bromo, iodo, trifluoromethyl, cyano or nitro; X is phenylene optionally bearing a substituent selected from methyl, ethyl, methoxy, ethoxy, isopropoxy, fluoro, chloro, bromo, iodo, trifluoromethyl, cyano and nitro, or X is a direct bond between the adjacent phenyl and methylene groups; $R^6$ is hydrogen or a residue derived from a (1-6C)alkanol, or phenol or glycerol; and $R^7$ is methyl, ethyl, propyl, isopropyl, butyl, pentyl, cyclobutyl, cyclopentyl, cyclohexyl or phenyl; and wherein any of said phenyl moieties may be unsubstituted or bear one or two substituents independently selected from methyl, ethyl, methoxy, ethoxy, fluoro, chloro, bromo, cyano and trifluoromethyl.

3. A compound as claimed in claim 1 wherein $R^1$ is hydrogen, (1-8C)alkyl, trifluoromethyl, (3-8C)cycloalkyl, (3-8C)cycloalkyl(1-4C)alkyl, phenyl or phenyl(-1-4C)alkyl; and $R^3$, $R^4$ and $R^5$ are independently selected from hydrogen, (1-4C)alkyl, (1-4C)alkoxy, halogeno, trifluoromethyl, cyano and nitro; or when ring B is a pyridine moiety, $R^3$ and $R^4$ may optionally together form a (1-4C)alkylenedioxy group.

4. A naphthyridine of the formula III

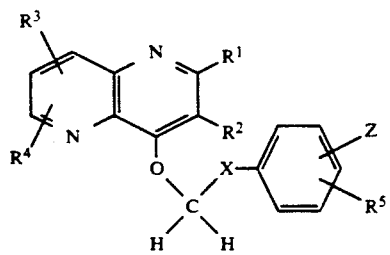

III wherein $R^1$, $R^2$, $R^3$, $R^4$, $R^5$, X and Z have any of the meanings defined in claim 1; or a physiologically acceptable salt thereof.

5. A naphthyridine of the formula III

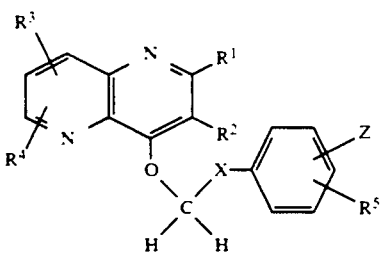

wherein $R^1$, $R^2$, $R^3$, $R^4$, $R^5$, X and Z have any of the meanings defined in claim 2; or a physiologically acceptable salt thereof.

6. A naphthyridine of the formula III

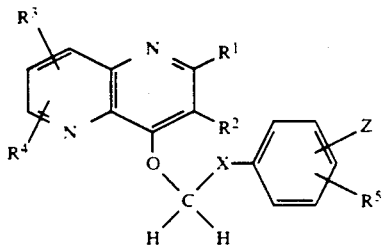

wherein $R^1$, $R^2$, $R^3$, $R^4$, $R^5$, X and Z have any of the meanings defined in claim 3; or a physiologically acceptable salt thereof.

7. A naphthyridine as claimed in claim 4, 5 or 6 wherein one of $R^3$ and $R^4$ is selected from hydrogen, (1-4C)alkyl, (1-4C)alkoxy and fluoro(1-4C)alkoxy and is attached at the 6-position of the naphthyridine ring; and the other of $R^3$ and $R^4$ is hydrogen.

8. A compound as claimed in claim 1, 4, 5 or 6 wherein X is p-phenylene and Z is 1H-tetrazol-5-yl attached ortho to the group X.

9. A compound of the formula I as claimed in claim 1 selected from:

2-ethyl-4-[(2'-(1H-tetrazol-5-yl)biphenyl-4-yl)methoxy]-1,5-naphthyridine;

2-ethyl-6-methoxy-4-[(2'-(1H-tetrazol-5-yl)biphenyl-4-yl)methoxy]-1,5-naphthyridine;

6-ethoxy-2-ethyl-4-[(2'-(1H-tetrazol-5-yl)biphenyl-4-yl)methoxy]-1,5-naphthyridine;

2-ethyl-6-isopropoxy-4-[(2'-(1H-tetrazol-5-yl)biphenyl-4-yl)methoxy]-1,5-naphthyridine;

2-ethyl-6-(2,2,2-trifluoroethoxy)-4-[(2'-(1H-tetrazol-5-yl)biphenyl-4-yl)methoxy]-1,5-naphthyridine; and 2-ethyl-6-methyl-4-[(2'-(1H-tetrazol-5-yl)biphenyl-4-yl)methoxy]-1,5-naphthyridine;

and the physiologically acceptable salts thereof.

10. A salt as claimed in claim 1 which is selected from salts with acids forming physiologically acceptable anions and, for those compounds of formula I which are acidic, alkali metal, alkaline earth metal, aluminium and ammonium salts, and salts with organic bases affording physiologically acceptable cations.

11. A method for antagonising one or more of the actions of angiotensin II in a warm-blooded animal requiring such treatment which comprises administering to said animal an antagonistically effective amount of a compound of formula I, or a physiologically acceptable salt thereof, as defined in claim 1.

12. A pharmaceutical composition which comprises a compound of the formula I or III, or a physiologically acceptable salt thereof, as claimed in claim 1 or 4, together with a pharmaceutically acceptable diluent or carrier.

13. A compound of the formula V

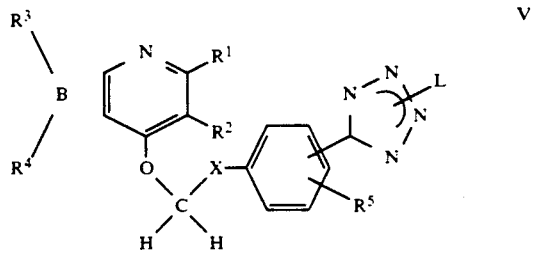

wherein ring B, $R^1$, $R^2$, $R^3$, $R^4$, $R^5$ and X have any of the meanings defined in claim 1, and L is a protecting group.

* * * * *